United States Patent

Dorigatti et al.

Patent Number: 5,520,916
Date of Patent: May 28, 1996

[54] NON-WOVEN FABRIC MATERIAL COMPRISING HYALURONIC ACID DERIVATIVES

[75] Inventors: Franco Dorigatti, Trento; Lanfranco Callegaro, Padova; Aurelio Romeo, Rome, all of Italy

[73] Assignee: M.U.R.S.T. (Italian Ministry for Universities and Scientific and Technological Research), Rome, Italy

[21] Appl. No.: 992,700

[22] Filed: Dec. 18, 1992

[30] Foreign Application Priority Data

Dec. 18, 1991 [IT] Italy ................. PD91A0229

[51] Int. Cl.⁶ ............... A61K 9/70; A61L 31/00
[52] U.S. Cl. ............... 424/402; 424/404; 424/444; 428/113; 428/224; 428/280; 428/288; 428/289; 602/45
[58] Field of Search ............... 424/401, 444, 424/402, 404; 428/113, 280, 289, 224, 288; 606/230; 602/45

[56] References Cited

U.S. PATENT DOCUMENTS

| | | | |
|---|---|---|---|
| 4,280,954 | 7/1981 | Yannas et al. | 260/123.7 |
| 4,851,521 | 7/1989 | Della Valle et al. | 536/55.1 |
| 4,965,353 | 10/1990 | Della Valle et al. | 536/55.1 |
| 5,147,861 | 9/1992 | Della Valle et al. | 536/55.1 |

FOREIGN PATENT DOCUMENTS

| | | |
|---|---|---|
| 0138572 | 4/1985 | European Pat. Off. . |
| 0216453 | 4/1987 | European Pat. Off. . |
| 0251905 | 1/1988 | European Pat. Off. . |
| 0265116 | 4/1988 | European Pat. Off. . |
| 0341745 | 11/1989 | European Pat. Off. . |
| 2-268765 | 11/1990 | Japan . |
| 2103993 | 3/1983 | United Kingdom . |
| 9117744 | 11/1991 | WIPO . |
| 9213579 | 8/1992 | WIPO . |

OTHER PUBLICATIONS

P. H. Weigel et al J. Theor. Biol., vol. 119 (1986) pp. 219–234.
R. H. Cundiff et al Analytical Chemistry, vol. 33 (1961) pp. 1028–1030.
Database WPIL, Week 8709, Derwent Publications Ltd., London, GB, AN 87–062629 & ZA, A, 8 605 071 (FIDIA S.P.A.) 8 Jul. 1987
Cortivo et al., Biomaterials 1991, vol. 12 Oct., pp. 727–730.

*Primary Examiner*—Edward J. Webman
*Attorney, Agent, or Firm*—Birch, Stewart, Kolasch & Birch

[57] ABSTRACT

Biomaterials are disclosed comprised of biodegradable, biocompatible, and bioabsorbable nonwoven fabric materials for use in surgery for the guided regeneration of tissues. The non-woven fabric materials are comprised of threads embedded in a matrix, wherein both the matrix and the threads can be comprised of esters of hyaluronic acid, used singly or in combination, or esters of hyaluronic acid in combination with esters of alginic acid or other polymers.

24 Claims, 2 Drawing Sheets

NON-WOVEN FABRIC MATERIAL COMPRISING HYALURONIC ACID DERIVATIVES

BACKGROUND OF THE INVENTION

1. Field of the Invention

The present invention relates to a new non-woven fabric material comprising hyaluronic acid derivatives, methods of production thereof, and methods of using said material in medical and pharmaceutical applications.

2. Description of Related Art

Hyaluronic acid is a natural heteropolysaccharide composed of alternating residues of D-glucuronic acid and N-acetyl-D-glucosamine. It is a linear polymer with a molecular weight of between 50,000 and 13,000,000 depending upon the source from which it is obtained, and the preparation and determination methods employed. It is present in nature in pericellular gels, in the fundamental substance of connective tissues of vertebrate organisms of which it is one of the main components, in the synovial fluid of joints, in the vitreous humor, in human umbilical cord tissues, and in cocks' combs.

There are known, specific fractions of hyaluronic acid with definite molecular weights that do not present inflammatory activity, and which can therefore be used to facilitate wound healing, to substitute for the endobulbar fluids, or which can be employed in therapy for joint pathologies by intra-articular injections, as described in European Patent No. 0 138 572 granted to Applicants on Jul. 25, 1990.

Also known are hyaluronic acid esters, wherein all or some of the carboxy groups of the acid are esterified, and their use in the pharmaceutical and cosmetic fields and in the area of biodegradable plastic materials, as described in U.S. Pat. Nos. 4,851,521 and 4,965,353 granted to Applicants.

Hyaluronic acid is known to play a fundamental role in tissue repair processes, especially in the first stages of granulation, by stabilizing the coagulation matrix and controlling its degradation, favoring the recruitment of inflammatory cells such as polymorphonuclear leukocytes and monocytes, of mesenchymal cells such as fibroblasts and endothelial cells, and in orienting the subsequent migration of epithelial cells.

It is known that the application of solutions of hyaluronic acid can accelerate healing in patients affected by bedsores, wounds and burns. The role of hyaluronic acid in the various phases that constitute tissue repair processes has been described, by the construction of a theoretical model, by Weigel P. H. et al.: "A model for the role of hyaluronic acid and fibrin in the early events during the inflammatory response and wound healing," *J. Theor. Biol.*, 119: 219, 1986.

Studies aimed at obtaining manufactured products to apply to the skin, composed of hyaluronic acid esters as such or in mixtures with other polymers have led to the creation of various types of products. Among these are fabrics, such as gauzes of varying thickness (number of threads per centimeter), with varying dimensions, and with threads of varying denier (weight per 9000 meters of thread). Films of widely varying thickness have been proposed, as described in U.S. Pat. Nos. 4,851,521 and 4,965,353.

The use of such materials as skin coverings is limited by their stiffness, which is more or less determined according to how they were made. It is always a problem, however, when the material has to mould itself to the surface to be covered. Another drawback to the use of such materials is their poor absorbability, if any, of liquids such as solutions of disinfectants, antibiotics, antiseptics, antimicotics, proteins or wound healing substances in general, even when these are neither thick nor viscous.

SUMMARY OF THE INVENTION

Accordingly, it is an object of the present invention to provide pliable non-woven fabric materials.

It is also an object of the present invention to provide a method for the preparation of such non-woven fabric materials.

The non-woven fabric materials of the present invention are composed of hyaluronic acid esters, used singly or in combination with one another, or with other types of polymers. Such materials are particularly soft, and can be easily impregnated with various kinds of liquids.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DETAILED DESCRIPTION OF THE INVENTION

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited in the present application are herein incorporated by reference in their entirety.

The objects of the present invention are achieved by non-woven fabrics according to the present invention weighing between about 20 gr/mq and about 500 gr/mq, and between about 0.2 mm and about 5 mm in thickness. The non-woven fabric can be described as a web composed of a large quantity of fibers varying in diameter between about 12 and about 60 micrometers and in length between about 5 mm and about 100 mm, joined together by chemical coagulation or mechanical means, or with the aid of cohesive material.

The non-woven fabric comprises hyaluronic acid esters used singly or in mixtures with each other in varying ratios. Moreover, the present non-woven fabrics can comprise mixtures of fibers of hyaluronic acid esters with fibers of natural polymers, varying in ratio from 1 to 100% of the total, such as collagen, or coprecipitates of collagen and glycosaminoglycans, cellulose, polysaccharides in gel form such as chitin, chitosan, pectin or pectic acid, agar, agarose, xanthan gum, gellan, alginic acid or alginates, polymannan or polyglycans, starches, natural gums, or fibers obtained from semisynthetic derivatives of natural polymers such as collagen cross-linked with agents such as aldehydes or precursors of the same, dicarboxylic acids or halides of the same, diamines, derivatives of cellulose, alginic acid, starch, hyaluronic acid, chitin or chitosan, gellan, xanthan, pectin, or pectic acid, polyglycans, polymannan, agar, agarose, natural gums, glycosaminoglycans, or fibers obtained from synthetic polymers, such as polylactic acid, polyglycolic acid or copolymers of the same or their derivatives, polydioxanes, polyphosphazenes, polysulfone resins, and polyurethane resins.

The non-woven fabrics of the present invention possessing the above-mentioned characteristics can be produced from multifilaments produced by the usual wet and dry spinning methods and then cut into the desired lengths. The mass of fibers is fed into a carding machine which makes it into staples. The staples are then fed into a cross lapper, from which they emerge as webs of a specific weight.

The web can undergo chemical or mechanical cohesive treatment such as soaking in solvents and subsequent coagulation, needle punching treatment, treatment with bonding agents of the same material as constitutes the non-woven fabric, or of a different material, etc.

With respect to mechanical cohesive treatment, the principal of reinforcement of the fibrous web is based on the entangling of the fibers and the increased fiber friction obtained by the consolidation of the fibrous web. The fibers are entangled by piercing the web vertically with felting needles. These needles are mounted in machines, and the fibrous web is fed to the needling machine for needling, and finally to a structuring machine, which carries out the surface structuring.

Figure 1:
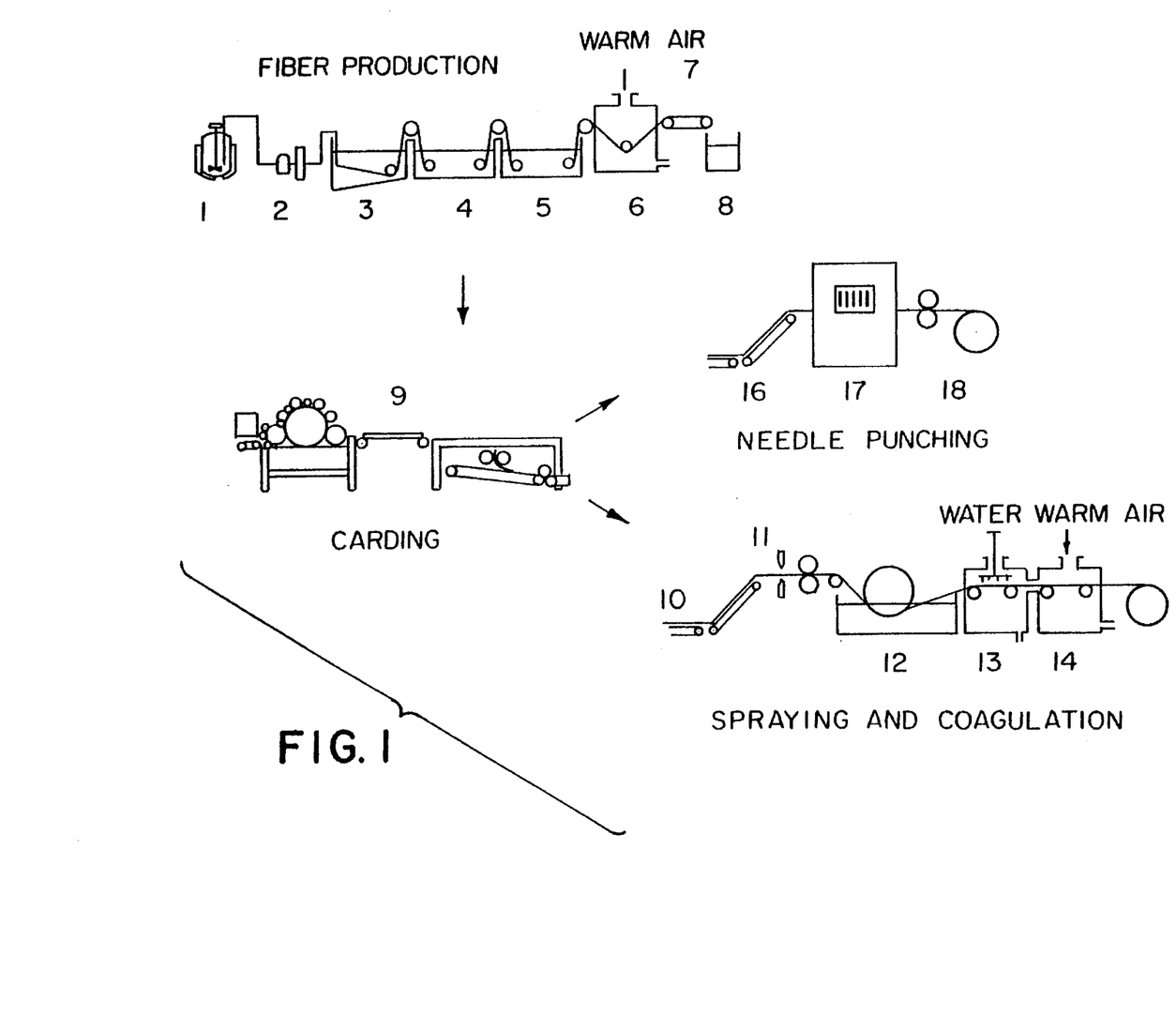
FIG. 1 is a schematic diagram illustrating the steps involved in the production of the non-woven fabric material of the present invention.

With respect to treatments with bonding agents, chemical cohesive treatment with bonding agents is performed on the fibrous web when it emerges from the carding machine (FIG. 1, detail 9). The purpose of this treatment is to fix the fibers at their contact points. In the case of non-woven fabrics composed essentially of hyaluronic acid esters, this is achieved by spraying (11) the fibrous web emerging from the carding machine with a solution of hyaluronic acid esters in, for example, dimethylsulfoxide. The dimethylsulfoxide, being a solvent for the fibers comprising the web, dissolves them, and "fuses" them in the subsequent coagulation bath (12). The web thus fixed is then washed (13) and dried (14).

The coagulation baths 3 and 15 are stainless steel, and are in the form of an upturned triangle so that the extracted solubilization material being formed can be kept in contact with fresh coagulation solvent.

The coagulation process is essentially an extraction process by which, from a solution of polymer and solvent, the extraction of the solubilization solvent and the solidification of the polymer can be effected by the addition of a second solvent, for example ethanol, in which the solubilization solvent, for example dimethylsulfoxide, is soluble, and the polymer is insoluble.

The above-described treatments have the effect of fixing the fibers one to the other so as to produce a structure composed of haphazardly placed, matted fibers, constituting a soft, resistant material.

The present invention therefore relates to a new class of products, non-woven fabrics, to be used in the medical/pharmaceutical field as skin coverings. These fabric materials are totally or partially biocompatible and bioabsorbable, and are composed of hyaluronic acid esters used singly or in mixtures with each other, or with other natural or synthetic polymers. Such materials are characterized by their softness, and by their ability to absorb liquids.

Such non-woven fabrics can be impregnated with, among other things, solutions of antibiotics, antiseptics, antimicotics or proteins. The term "non-woven fabric" covers in practice materials such as webs and felts, etc., composed of a large quantity of fibers, chemically or mechanically stuck together. The material has the appearance of a fabric, even though it is not woven in the strict sense of the word.

For purely illustrative purposes, described hereafter are some examples of how the non-woven fabric material of the present invention can be produced.

THE ESTERS OF HYALURONIC ACID

Esters of hyaluronic acid useful in the present invention are esters of hyaluronic acid with aliphatic, araliphatic, cycloaliphatic or heterocyclic alcohols, in which are esterified all (so-called "total esters") or only a part (so-called "partial esters") of the carboxylic groups of the hyaluronic acid, and salts of the partial esters with metals or with organic bases, biocompatible or acceptable from a pharmacological point of view.

The useful esters include esters which derive from alcohols which themselves possess a notable pharmacological action. The saturated alcohols of the aliphatic series or simple alcohols of the cycloaliphatic series are useful in the present invention.

In the above mentioned esters in which some of the carboxylic acid groups remain free (i.e., partial esters), these may be salified with metals or organic bass, such as with alkaline or alkaline earth metals or with ammonia or nitrogenous organic bases.

Most of the esters of hyaluronic acid ("HY"), unlike HY itself, present a certain degree of solubility in organic solvents. This solubility depends on the percentage of esterified carboxylic groups and on the type of alkyl group linked with the carboxyl. Therefore, an HY compound with all its carboxylic groups esterified presents, at room temperature, good solubility for example in dimethylsulfoxide (the benzyl ester of HY dissolves in DMSO in a measure of 200 mg/ml). Most of the total esters of HY present also, unlike HY and especially its salts, poor solubility in water and are essentially insoluble in water. The solubility characteristics, together with particular and notable viscoelastic properties, make the HY esters particularly preferred for use in composite membranes.

Alcohols of the aliphatic series to be used as esterifying components of the carboxylic groups of hyaluronic acid for use in composite membranes according to the present invention are for example those with a maximum of 34 carbon atoms, which may be saturated or unsaturated and which may possibly also be substituted by other free functional or functionally modified groups, such as amine, hydroxyl, aldehyde, ketone, mercaptan, or carboxyl groups or by groups derived from these, such as hydrocarbyl or dihydrocarbylamine groups (from now on the term "hydrocarbyl" will be used to refer not only to monovalent radicals of hydrocarbons such as the $C_nH_{2n+1}$ type, but also bivalent or trivalent radicals, such as "alkylenes" $C_nH_{2n-1}$ or "alkylidenes" $C_nH_{2n}$), ether or ester groups, acetal or ketal groups, thioether or thioester groups, and esterified carboxyl or carbamide groups and carbamide substituted by one or more hydrocarbyl groups, by nitrile groups or by halogens.

Of the above mentioned groups containing hydrocarbyl radicals, these are preferably lower aliphatic radicals, such as alkyls, with a maximum of 6 carbon atoms. Such alcohols may also be interrupted in the carbon atom chain by heteroatoms, such as oxygen, nitrogen and sulfur atoms. Preferred are alcohols substituted with one or two of the said functional groups.

Alcohols of the above mentioned group which are preferably used are those with a maximum of 12, and especially 6 carbon atoms, and in which the hydrocarbyl atoms in the above mentioned amine, ether, ester, thioether, thioester, acetal, ketal groups represent alkyl groups with a maximum of 4 carbon atoms, and also in the esterified carboxyl or substituted carbamide groups the hydrocarbyl groups are alkyls with the same number of carbon atoms, and in which in the amine or carbamide groups may be alkylenamine or alkylenecarbamide groups with a maximum of 8 carbon atoms. Of these alcohols, specifically preferred are saturated and nonsubstituted alcohols, such as the methyl, ethyl, propyl, and isopropyl alcohols, normal butyl alcohol, isobutyl alcohol, tertiary butyl alcohol, the amyl, pentyl, hexyl, octyl, nonyl and dodecyl alcohols and, above all, those with a linear chain, such as normal octyl and dodecyl alcohols. Of the substituted alcohols of this group, the bivalent alcohols are useful, such as ethyleneglycol, propyleneglycol and butyleneglycol, the trivalent alcohols such as glycerine, the aldehyde alcohols such as tartronic alcohol, the carboxylic alcohols such as lactic acids, for example glycolic acid, malic acid, the tartaric acids, citric acid, the aminoalcohols, such as normal aminoethanol, aminopropanol, normal aminobutanol and their dimethylated and diethylated derivatives in the amine function, choline, pyrrolidinylethanol, piperidinylethanol, piperazinylethanol and the corresponding derivatives of normal propyl or normal butyl alcohol, monothioethyleneglycol or its alkyl derivatives, such as the ethyl derivative in the mercaptan function.

Of the higher saturated aliphatic alcohols, preferred are cetyl alcohol and myricyl alcohol, but for the aim of the present invention the higher unsaturated alcohols with one or two double bonds, are especially important, such as especially those contained in many essential oils and related to terpenes, such as citronellol, geraniol, nerol, nerolidol, linalool, farnesol, and phytol. Of the unsaturated lower alcohols it is necessary to consider allyl alcohol and propargyl alcohol. Of the araliphatic alcohols, preferred are those with only one benzene residue and in which the aliphatic chain has a maximum of 4 carbon atoms, which the benzene residue can be substituted by between 1 and 3 methyl or hydroxyl groups or by halogen atoms, especially by chlorine, bromine and iodine, and in which the aliphatic chain may be substituted by one or more functions chosen from the group containing fee amine groups or mono- or dimethylated or by pyrrolidine or piperidine groups. Of these alcohols, most preferred are benzyl alcohol and phenetyl alcohol.

The alcohols of the cycloaliphatic or aliphatic-cycloaliphatic series may derive from mono- or polycyclic hydrocarbons, may preferably have a maximum of 34 carbon atoms, may be unsubstituted and may contain one or more substituents, such as those mentioned above for the aliphatic alcohols. Of the alcohols derived from cyclic monoannular hydrocarbons, preferred are those with a maximum of 12 carbon atoms, the rings with preferably between 5 and 7 carbon atoms, which may be substituted for example by between one and three lower alkyl groups, such as methyl, ethyl, propyl or isopropyl groups. As specific alcohols of this group the following are most preferred: cyclohexanol, cyclohexanediol, 1,2,3-cyclohexanetriol and 1,3,5-cyclohexanetriol (phloroglucitol), inositol, and the alcohols which derive from p-methane such as carvomenthol, menthol, and $\alpha$-$\gamma$terpineol, 1-terpineol, 4-terpineol and piperitol, or the mixture of these alcohols known as "terpineol", 1,4- and 1,8 terpin. Of alcohols which derive from hydrocarbons with condensed rings, such as those of the thujane, pinane or comphane, the following are preferred: thujanol, sabinol, pinol hydrate, D and L-borneol and D and L-isoborneol.

Aliphatic-cycloaliphatic polycyclic alcohols to be used for the esters of the present invention are sterols, cholic acids and steroids, such as sexual hormones and their synthetic analogues, especially corticosteroids and their derivatives. It is therefore possible to use: cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin and their alkylate derivatives, as well as their ethynyl or propynyl derivatives in position 17, such as 17$\alpha$-ethynl-estradiol or 7$\alpha$-methyl-17$\alpha$-ethynyl-estradiol, pregnenolone, pregnanediol, testosterone and its derivatives, such as 17$\alpha$-methyltestosterone, 1,2-dehydrotestosterone and 17$\alpha$-methyl-1,2-dehydrotesterone, the alkynylate derivatives in position 17 of testosterone and 1,2-dehydrotestosterone, such as 17$\alpha$-ethynyltestosterone, 17$\alpha$-propynyltestosterone, norgestrel, hydroxyprogesterone, corticosterone, deoxycorticosterone, 19-nortestosterone, 19-nor-17$\alpha$-methyltestosterone and 19-nor-17$\alpha$-ethynyltestosterone, antihormones such as cyproterone, cortisone, hydrocortisone, prednisone, prednisolone, fluorocortisone, dexamethasone, betamethasone, paramethasone, flumethasone, fluocinolone, fluprednylidene, clobetasol, beclomethasone, aldosterone, deoxycorticosterone, alfaxolone, alfadolone, and bolasterone. As esterifying components for the esters of the present invention the following are useful: genins (aglycones) of the cardioactive glucosides, such as digitoxigenin, gitoxigenin, digoxigenin, strophanthidin, tigogenin and saponins.

Other alcohols to be used according to the invention are vitamins, such as axerophthol, vitamins $D_2$ and $D_3$, aneurine, lactoflavine, ascorbic acid, riboflavine, thiamine, and pantothenic acid.

Of the heterocyclic acids, the following can be considered as derivatives of the above mentioned cycloaliphatic or aliphatic-cycloaliphatic alcohols if their linear or cyclic chains are interrupted by one or more, for example by between one and three heteroatoms, for instance chosen from the group formed by —O—, —S—, —N, and —NH—, and in these, there may be one or more unsaturated bonds, for example double bonds, in particular between one and three, thus including also heterocyclic compounds with aromatic structures. For example the following should be mentioned: furfuryl alcohol, alkaloids and derivatives such as atropine, scopolamine, cinchonine, la cinchonidine, quinine, morphine, codeine, nalorphine, N-butylscopolammonium bromide, ajmaline; phenylethylamines such as ephedrine, isoproterenol, epinephrine; phenothiazine drugs such as perphenazine, pipothiazine, carphenazine, homofenazine, a cetophenazine, fluophenazine, and N-hydroxyethylpromethazine chloride; thioxanthene drugs such as flupenthixol and clopenthixol; anticonvulsants such as meprophendiol; antipsychotics such as opipramol; antiemetics such as oxypendyl; analgesics such as carbetidine and phenoperidine and methadol; hypnotics such as etodroxizine; anorexics such as benzidrol and diphemethoxidine; minor tranquilizers such as hydroxyzine; muscle relaxants such as cinnamedrine, diphylline, mephenesin, methocarbamol, chlorphenesin, 2,2-diethyl-1,3-propanediol, guaifenesin, hydrocilamide; coronary vasodilators such as dipyridamole and oxyfedrine; adrenergic blockers such as propanolol, timolol, pindolol, bupranolol, atenolol, metroprolol, practolol; antineoplastics such as 6-azauridine, cytarabine, floxuridine; antibiotics such as chloramphenicol, thiamphenicol, erythromycin, oleandomycin, lincomycin; antivirals such as idoxuridine; peripheral vasodilators such as isonicotinyl alcohol; carbonic anhydrase inhibitors such as sulocarbilate; antiasthmatics and antiinflammatories such as tiaramide; sulfamidics such as 2-p-sulfanilonoethanol.

In some cases hyaluronic acid esters may be of interest where the ester groups derive from two or more therapeutically active hydroxylic substances, and naturally all possible variants may be obtained. Especially interesting are the substances in which two types of different ester groups deriving from drugs of a hydroxyl character are present and in which the remaining carboxyl groups are free, salified with metals or with a base, possibly also the bases being themselves therapeutically active, for example with the same or similar activity as that of the esterifying component. In particular, it is possible to have hyaluronic esters deriving on the one hand from an antiinflammatory steroid, such as one of those mentioned previously, and on the other hand from a vitamin, from an alkaloid or from an antibiotic, such as one of those listed.

METHOD OF PREPARING HY ESTERS OF THE INVENTION

Method A

The esters of hyaluronic acid may be prepared by methods known per se for the esterification of carboxylic acids, for example by treatment of free hyaluronic acid with the desired alcohols in the presence of catalyzing substances, such as strong inorganic acids or ionic exchangers of the acid type, or with an etherifying agent capable of introducing the desired alcoholic residue in the presence of inorganic or organic bases. As esterifying agents it is possible to use those known in literature, such as especially the esters of various inorganic acids or of organic sulphonic acids, such as hydracids, that is hydrocarbyl halogenides, such as methyl or ethyl iodide, or neutral sulphates or hydrocarbyl acids, alfites, carbonates, silicates, phosphites or hydrocarbyl sulfonates, such as methyl benzene or p-toluene-sulfonate or methyl or ethyl chlorosulfonate. The reaction may take place in a suitable solvent, for example an alcohol, preferably that corresponding to the alkyl group to be introduced in the carboxyl group. But the reaction may also take place in non-polar solvents, such as ketones, ethers, such as dioxane or aprotic solvents, such as dimethylsulphoxide. As a base it is possible to use for example a hydrate of an alkaline or alkaline earth metal or magnesium or silver oxide or a basic salt or one of these metals, such as a carbonate, and, of the organic bases, a tertiary azotized base, such as pyridine or collidine. In the place of the base it is also possible to use an ionic exchanger of the basic type.

Another esterification method employs the metal salts or salts with organic azotized bases, for example ammonium or ammonium substitute salts. Preferably, the salts of the alkaline or alkaline earth metals are used, but also any other metallic salt may be used. The esterifying agents are also in this case those mentioned above and the same applies to the solvents. It is preferable to use aprotic solvents, for example dimethylsulphoxide and dimethylformamide.

In the esters obtained according to this procedure or according to the other procedure described hereafter, free carboxylic groups of the partial esters may be salified, if desired, in a per se known manner.

Method B

The hyaluronic esters may also be prepared by a method which consists of treating a quaternary ammonium salt of hyaluronic acid with an etherifying agent, preferably in an aprotic organic solvent.

As organic solvents it is preferable to use aprotic solvents, such as dialkylsulphoxides, dialkylcarboxamides, such as in particular lower alkyl dialkylsulphoxides, especially dimethyl-sulphoxide, and lower alkyl dialkylamides of lower aliphatic acids, such as dimethyl or diethyl-formamide or dimethyl or diethylacetamide.

Other solvents however are to be considered which are not always aprotic, such as alcohols, ethers, ketones, esters, especially aliphatic or heterocyclic alcohols and ketones with a lower boiling point, such as hexafluoroisopropanol, trifluoroethanol, and N-methylpyrrolidone.

The reaction is effected preferably at a temperature range of between about 0° C. and 100° C., especially between about 25° C. and 75° C., for example at about 30° C.

The esterification is carried out preferably by adding by degrees the esterifying agent to the above mentioned ammonium salt to one of the above mentioned solvents, for example to dimethyl-sulphoxide.

As an alkylating agent it is possible to use those mentioned above, especially the hydrocarbyl halogens, for example alkyl halogens. As starting quaternary ammonium salts it is preferable to use the lower ammonium tetraalkylates, with alkyl groups preferably between 1 and 6 carbon atoms. Mostly, hyaluronate of tetrabutylammonium is used. It is possible to prepare these quaternary ammonium salts by reacting a metallic salt of hyaluronic acid, preferably one of those mentioned above, especially sodium or potassium salt, in aqueous solution with a salified sulphonic resin with a quaternary ammonium base.

One variation of the previously described procedure consists in reacting a potassium or sodium salt of hyaluronic acid, suspended in a suitable solution such as dimethylsulphoxide, with a suitable alkylating agent in the presence of catalytic quantities of a quaternary ammonium salt, such as iodide of tetrabutylammonium.

For the preparation of the hyaluronic acid esters, it is possible to use hyaluronic acids of any origin, such as for example the acids; extracted from the above mentioned natural starting materials, for example from cocks' combs. The preparation of such acids is described in literature: preferably, purified hyaluronic acids are used. Especially used are hyaluronic acids comprising molecular fractions of the integral acids obtained directly by extraction of the organic materials with molecular weights varying within a wide range, for example from about 90%–80% (MW=11.7–10.4 million) to 0.2% (MW=30,000) of the molecular weight of the integral acid having a molecular weight of 13 million, preferably between 5% and 0.2%. Such fractions may be obtained with various procedures described in literature, such as by hydrolyzing, oxydizing, enzymatic or physical procedures, such as mechanical or radiational procedures. Primordial extracts are therefore often formed during these same by publication procedures (for example see the article by Balazs et al. quoted above in "Cosmetics & Toiletries"). The separation and purification of the molecular fractions obtained are brought about by known techniques, for example by molecular filtration.

Additionally useful are purified fractions obtainable from hyaluronic acid, such as for example the ones described in European Patent Publn. No. 0138572.

The salification of HY with the above metals, for the preparation of starting salts for the particular esterification procedure described above, is performed in a per se known manner, for example by reacting HY with the calculated base quantity, for example with alkaline hydrates or with basic salts of such metals, such as carbonates or bicarbonates.

In the partial esters it is possible to salify all the remaining carboxylic groups or only part of them, dosing the base quantities so as to obtain the desired stoichiometric degree of salification. With the correct degree of salification it is possible to obtain esters with a wide range of different dissociation constants and which therefore give the desired pH, in solution or "in situ" at the time of therapeutic application.

PREPARATION EXAMPLES

The following exemplify the preparation of hyaluronic acid esters useful in the composite membranes of the present invention.

EXAMPLE 1

Preparation of the (Partial) Propyl Ester of
Hyaluronic Acid (HY)—50% of the Esterified
Carboxylic Groups—50% of the Salified
Carboxylic Groups (Na)

12.4 g of HY tetrabutylammonium salt with a molecular weight 170,000 corresponding to 20 m.Eq. of a monomeric unit are solubilized in 620 ml of dimethylsulfoxide at 25° C., 1.8 g (10.6 m.Eq.) of propyl iodide are added and the resulting solution is kept at a temperature of 30° for 12 hours.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water (5:1) and three times with 500 ml of acetone and finally vacuum dried for 24 hours at 30° C. 7.9 g of the partial propyl ester compound in the title are obtained. Quantitative determination of the ester groups is carried out using the method of R. H. Cundiff and P. C. Markunas [Anal. Chem. 33, 1028–1030, (1961)].

EXAMPLE 2

Preparation of the (Partial) Isopropyl Ester of
Hyaluronic Acid (HY)—50% of Esterified
Carboxylic Groups—50% of Salified Carboxylic
Groups (Na)

12.4 g of HY tetrabutylammonium salt with a molecular weight of 160,000 corresponding to 20 m.Eq. of a monomeric unit are solubilized in 620 ml of dimethylsulfoxide at 25° C., 1.8 g (10.6 m.Eq.) of isopropyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.8 g of the partial isopropyl ester compound in the title are obtained. Quantitative determination of the ester groups is carried out using the method of R. H. Cundiff and P. C. Markunas [Anal. Chem. 33, 1028–1030 (1961)].

EXAMPLE 3

Preparation of the (Partial) Ethyl Ester of
Hyaluronic Acid (HY)—75% of Esterified
Carboxylic Groups—25% of Salified Carboxylic
Groups (Na)

12.4 g of HY tetrabutylammonium salt with a molecular weight of 250,000 corresponding to 20 m.Eq. of a monomeric unit are solubilized in 620 ml of dimethylsulfoxide at 25° C., 2.5 g (15.9 m.Eq.) of ethyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.9 g of the partial ethyl ester compound in the title are obtained. Quantitative determination of the ester groups is carried out using the method of R. H. Cundiff and P. C. Markunas [Anal. Chem. 33, 1028–1030, (1961)].

EXAMPLE 4

Preparation of the (Partial) Methyl Ester of
Hyaluronic Acid (HY)—75% of Esterified
Carboxylic Groups—25% of Salified Carboxylic
Groups (Na)

12.4 g of HY tetrabutylammonium salt with a molecular weight of 80,000 corresponding to 20 m.Eq. of a monomeric unit are solubilized in 620 ml of dimethylsulfoxide at 25° C., 2.26 g (15.9 m.Eq.) of methyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 7.8 g of the partial methyl ester compound in the title are obtained. Quantitative determination of the ester groups is carried out using the method of R. H. Cundiff and P. C. Markunas [Anal. Chem. 33, 1028–1030 (1961)].

EXAMPLE 5

Preparation of the Methyl Ester of Hyaluronic Acid (HY)

12.4 g of HY tetrabutylammonium salt with a molecular weight of 120,000 corresponding to 20 m.Eq. of a monomeric unit are solubilized in 620 ml of dimethylsulfoxide at 25° C., 3 g (21.2 m.Eq.) of methyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

EXAMPLE 6

Preparation of the Ethyl Ester of Hyaluronic Acid (HY)

12.4 g of HY tetrabutylammonium salt with a molecular weight of 85,000 corresponding to 20 m.Eq. of a monomeric unit are solubilized in 620 ml of dimethylsulfoxide at 25° C., 3.3 g (21.2 m.Eq.) of ethyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8 g of the ethyl ester product in the title are obtained. Quantitative determination of the ester groups is carried out using the method of R. H. Cundiff and P. C. Markunas [Anal. Chem. 33, 1028–1030 (1961)].

EXAMPLE 7

Preparation of the Propyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 3.6 g (21.2 m.Eq.) of propyl iodide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty-four hours at 30° C.

8.3 g of the propyl ester product in the title are obtained. Quantitative determination of the ester groups is carried out using the method of R. H. Cundiff and P. C. Markunas [Anal. Chem. 33, 1028–1030 (1961)].

EXAMPLE 8

Preparation of the (Partial) Butyl Ester of Hyaluronic Acid (HY)—50% of Esterified Carboxylic Groups—50% of Salified Carboxylic Groups (Na)

12.4 g of HY tetrabutylammonium salt with a molecular weight of 620,000 corresponding to 20 m.Eq. of a monomeric unit are solubilized in 620 ml of dimethylsulfoxide at 25° C., 1.95 g (10.6 m.Eq.) of n-butyl iodide are added and the resulting solution is kept for 12 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 8 g of the partial butyl ester compound in the title are obtained. Quantitative determination of the ester groups is carried out using the method of R. H. Cundiff and P. C. Markunas [Anal. Chem. 33, 1028–1030 (1961)].

EXAMPLE 9

Preparation of the (Partial) Ethoxycarbonylmethyl Ester of Hyaluronic Acid (HY)—75% of Esterified Carboxylic Groups—25% of Salified Carboxylic Groups (Na)

12.4 g of HY tetrabutylammonium salt with a molecular weight of 180,000 corresponding to 20 m.Eq. of a monomeric unit are solubilized in 620 ml of dimethylsulfoxide at 25° C., 2 g of tetrabutylammonium iodide and 1.84 g (15 m.Eq.) of ethyl chloroacetate are added and the resulting solution of kept for 24 hours at 30° C.

A solution containing 62 ml of water and 9 g of sodium chloride is added and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 10 g of the partial ethoxycarbonyl methyl ester compound in the title are obtained.

Quantitative determination of the ethoxylic ester groups is carried out using the method of R. H. Cundiff and P. C. Markunas [Anal. Chem. 33, 1028–1030 (1961)].

EXAMPLE 10

Preparation of the N-Pentyl Ester of Hyaluronic Acid (HY)

12.4 g of HY tetrabutylammonium salt with a molecular weight of 620,000 corresponding to 20 m.Eq. of a monomeric unit are solubilized in 620 ml of dimethylsulfoxide at 25° C., 3.8 g (25 m.Eq.) of n-pentyl bromide and 0.2 g of iodide tetrabutyl-ammonium are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.7 g of the n-pentyl ester product in the title are obtained. Quantitative determination of the ester groups is carried out using the method described on pages 169–172 of Siggia S. and Hann J. G. "Quantitative organic analysis via functional groups" 4th Edition, John Wiley and Sons.

EXAMPLE 11

Preparation of the Isopentyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethysulfoxide at 25° C., 3.8 g (25 m.Eq.) of isopentyl bromide and 0.2 g of tetrabutylammonium iodide are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

8.6 g of the isopentyl ester product featured in the title are obtained. Quantitative determination of the ester groups is carried out according to the method described on pages 169–172 of Siggia S. and Hanna J. G. "Quantitative organic analysis via functional groups" 4th Edition, John Wiley and Sons.

EXAMPLE 12

Preparation of the Benzylester of Hyaluronic Acid (HY)

12.4 g of HY tetrabutylammonium salt with a molecular weight of 170,000 corresponding to 20 m.Eq. of a monomeric unit are solubilized in 620 ml of dimethysulfoxide at 25° C., 4.5 g (25 m.Eq.) of benzyl bromide and 0.2 g of tetrabutylammonium iodide are added, the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for twenty four hours at 30° C.

9 g of the benzyl ester product in the title are obtained. Quantitative determination of the ester groups is carried out according to the method described on pages 169–172 of Siggia S. and Hanna J. G. "Quantitative organic analysis via functional groups" 4th Edition, John Wiley and Sons.

EXAMPLE 13

Preparation of the β-Phenylethyl Ester of Hyaluronic Acid (HY)

12.4 g of HY tetrabutylammonium salt with a molecular weight of 125,000 corresponding to 20 m.Eq. of a monomeric unit are solubilized in 620 ml of dimethylsulfoxide at 25° C., 4.6 g (25 m.Eq.) of 2-bromoethylbenzene and 185 mg of tetrabutylammonium iodide are added, and the solution is kept for 12 hours at 30° C.

The resulting mixture is slowly poured into 3,500 ml of ethyl acetate under constant agitation. A precipitate is thus formed which is then filtered and washed four times with 500 ml of ethyl acetate and finally vacuum dried for twenty four hours at 30° C.

9.1 g of the β-phenylethyl ester in the title are obtained. Quantitative determination of the ester groups is carried out according to the method described on page 168–172 of Siggia S., and hanna J. G. "Quantitative organic analysis via functional groups" 4th Edition, John Wiley and Sons.

EXAMPLE 14

Preparation of the Benzyl Ester of Hyaluronic Acid (HY)

3 g of the potassium salt of HY with a molecular weight of 162,000 are suspended in 200 ml of dimethylsulfoxide; 120 mg of tetrabutylammonium iodide and 2.4 g of benzyl bromide are added.

The suspension is kept in agitation for 48 hours at 30° C. The resulting mixture is slowly poured into 1,000 ml of ethyl acetate under constant agitation. A precipitate is formed which is filtered and washed four times with 150 ml of ethyl acetate and finally vacuum dried for twenty four hours at 30° C.

3.1 g of the benzyl ester product in the title are obtained. Quantitative determination of the ester groups is carried out according to the method described on pages 169–172 of Siggia S. and Hanna J. G. "Quantitative organic analysis via functional groups" 4th Edition, John Wiley and Sons.

EXAMPLE 15

Preparation of the (Partial Propyl) Ester of Hyaluronic Acid (HY)—85% of Esterified Carboxylic Groups—15% of Salified Carboxylic Groups (Na)

12.4 g of HY tetrabutylammonium salt with a molecular weight of 165,1000 corresponding to 20 m.Eq. of a monomeric unit are solubilized in 620 ml of dimethysulfoxide at 25° C., 2.9 g (17 m.Eq.) of propyl iodide are added and the resulting solution is kept for 12 hours at 30° C.

A solution is then added containing 62 ml of water and 9 g of sodium chloride and the resulting mixture is slowly poured into 3,500 ml of acetone under constant agitation. A precipitate is formed which is filtered and washed three times with 500 ml of acetone/water 5:1 and three times with acetone and finally vacuum dried for eight hours at 30° C.

The product is then dissolved in 550 ml of water containing 1.% of sodium chloride and the solution is slowly poured into 3,000 ml of acetone under constant agitation. A precipitate is formed which is filtered and washed twice with 500 ml of acetone/water 5:1 and three times with 500 ml of acetone and finally vacuum dried for 24 hours at 30° C. 8 g of the partial propyl ester compound in the title are obtained. Quantitative determination of the ester groups is carried out using the method of R. H. Cundiff and P. C. Markunas [Anal. Chem. 33, 1028–1030 (1961)].

EXAMPLE 16

Preparation of the N-Octyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.1 g (21.2 m.Eq.) of 1-bromooctane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the octyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

EXAMPLE 17

Preparation of the Isopropyl Ester of Hyaluronic Acid (HY)

12.4 g of HY tetrabutylammonium salt with a molecular weight of 170.000 corresponding to 20 m.Eq. of a monomeric unit are solubilized in 620 ml of dimethylsulfoxide at 25° C., 2.6 g (21.2 m.Eq.) of isopropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 8.3 g of the isopropyl ester product in the title are obtained. Quantitative determination of the ester groups is carried out using the method of R. H. Cundiff and P. C. Markunas (Anal. Chem. 33, 1028–1030, 1961).

EXAMPLE 18

Preparation of the 2,6-Dichlorobenzyl Ester of Hyaluronic Acid (HY)

12.4 g of HY tetrabutylammonium salt with a molecular weight of 170.000 corresponding to 20 m.Eq. of a monomeric unit are solubilized in 620 ml of dimethylsulfoxide at 25° C., 5.08 g (21.2 m.Eq.) of 2,6-dichlorobenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.7 g of the 2,6-dichlorobenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

EXAMPLE 19

Preparation of the 4-Terbutylbenzyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.81 g (21.2 m.Eq.) of 4-terbutylbenzyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.8 g of the 4-terbutylbenzyl ester product in the title are obtained. Quantitative determination of the ester groups is carried out using the method described in Siggia S. and Hanna J. G. "Quantitative organic analysis via functional groups" 4th Edition, John Wiley and Sons, pages 169–172.

EXAMPLE 20

Preparation of the Heptadecyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 6.8 g (21.2 M.Eq.) of Heptadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the Heptadecyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

EXAMPLE 21

Preparation of the Octadecyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 7.1 g (21.2 m.Eq.) of octadecyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 11 g of the octadecyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

EXAMPLE 22

Preparation of the 3-Phenylpropyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.22 g (21.2 m.Eq.) of 3-phenylpropyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the 3-phenylpropyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

EXAMPLE 23

Preparation of the 3,4,5-Trimethoxy-Benzyl Ester of Hyaluronic Acid (HY)

12.4 g of HY tetrabutylammonium salt with a molecular weight of 170,000 corresponding to 20 M.Eq. of a monomeric unit are solubilized in 620 ml of dimethylsulfoxide at 25° C., 4.6 g (21.2 m.Eq.) of 3,4,5-trimethoxybenzyl chloride are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 10 g of the 3,4,5-trimethoxybenzyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

EXAMPLE 24

Preparation of the Cinnamyl Ester of Hyaluronic Acid (HY)

12.4 g of Hy tetrabutylammonium salt with a molecular weight of 170,000 corresponding to 20 m.Eq. of a monomeric unit are solubilized in 620 ml of dimethylsulfoxide at 25° C., 4.2 9 (21.2 m.Eq.) of Cinnamyl bromide are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.3 g of the Cinnamyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

EXAMPLE 25

Preparation of the Decyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.7 g (21.2 m.Eq.) of 1-bromo decane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9.5 g of the Decyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

EXAMPLE 26

Preparation of the Nonyl Ester of Hyaluronic Acid (HY)

12.4 g of HY tetrabutylammonium salt with a molecular weight of 170,000 corresponding to 20 m.Eq. of a monomeric unit are solubilized in 620 ml of dimethylsulfoxide at 25° C., 4.4 g (21.2 m.Eq.) of 1-bromo nonane are added and the solution is kept for 12 hours at 30° C.

The resulting mixture is slowly poured into 3,500 ml of ethyl acetate under constant agitation. A precipitate is formed which is filtered and washed four times with 500 ml of ethyl acetate and finally vacuum dried for 24 hours at 30° C. 9 g of the Nonyl ester product in the title are obtained. Quantitative determination of the ester groups is carried out using the method described in Siggia S. and Hanna J. G. "Quantitative organic analysis via functional groups", 4th Edition, John Wiley and Sons, pages 169–172.

THE ESTERS OF ALGINIC ACID

The alginic acid esters which can be employed in the present invention can be prepared as described in EPA 0 251 905 A2 by starting with quaternary ammonium salts of alginic acid with an etherifying agent in a preferably aprotic organic solvent, such as dialkylsulfoxides, dialkylcarboxamides, such as in particular lower alkyl dialkylsulfoxides, above all dimethylsulfoxide, and lower alkyl dialkylamides of lower aliphatic acids, such as dimethyl or diethyl formamide or dimethyl or diethyl acetamide. It is possible, however, to use other solvents which are not always aprotic, such as alcohols, ethers, detones, esters, especially aliphatic or heterocyclic alcohols and ketones with a low boiling point, such as hexafluoroisopropanol and trifluoroethanol. The reaction is brought about preferably at a temperature of between about 0° and 100° C., and especially between about 25° and 75° C., for example at about 30° C.

Esterification is carried out preferably by gradually adding the esterifying agent to the above-mentioned ammonium salt dissolved in one of the solvents mentioned, for example in dimethylsulfoxide. As alkylating agents, those mentioned above can be used, especially hydrocarbyl halides, for example alkyl halides.

The preferred esterification process, therefore, comprises reacting, in an organic solvent, a quaternary ammonium salt of alginic acid with a stoichiometric quantity of a compound of the formula

A—X wherein A is selected from the group consisting of an aliphatic, araliphatic, cycloaliphatic, aliphatic-cycloaliphatic and heterocyclic radicals, and X is a halogen atom, and wherein said stoichiometric quantity of A—X is determined by the degree of esterification desired.

As starting quaternary ammonium salts, it is preferable to use lower ammonium tetraalkylates, the alkyl groups having preferably between 1 and 6 carbon atoms. Mostly, the alginate of tetrabutylammonium is used. These quaternary ammonium salts can be prepared by reacting a metal salt of alginic acid, preferably one of those mentioned above, especially the sodium or potassium salt, in aqueous solution with a sulfonic resin salified with the quaternary ammonium base.

One variation of the previously specified procedure consists of reacting a potassium or sodium salt of alginic acid, suspended in a suitable solution such as dimethylsulfoxide, with a suitable alkylating agent in the presence of a catalyzing quantity of a quaternary ammonium salt, such as tetrabutylammonium iodide. This procedure makes it possible to obtain the total esters of alginic acid.

To prepare new esters it is possible to use alginic acids of any origin. The preparation of these acids is described in literature. It is preferable to use purified alginic acids.

In the partial esters, it is possible to salify all the remaining carboxy groups or only part of these, dosing the base quantity so as to obtain the desired stoichiometric degree of salification. By correctly gauging the degree of salification, it is possible to obtain esters with a wide range of different dissociation constants, thereby giving the desired pH in solutions or "in situ" at the time of therapeutic application.

ALAFF 11, the benzyl ester of alginic acid, and ALAFF 7, the ethyl ester of alginic acid, are particularly useful in the present composite membranes.

EXAMPLE 27

A non-woven fabric comprising hyaluronic acid benzyl ester HYAFF 11, weighing 40 gr/mq, 0.5 mm thick, was produced by the following procedure (see FIG. 1).

A solution of HYAFF 11 in dimethylsulfoxide at a concentration of 135 mg/ml is prepared in a tank (1) and fed by a gear metering pump (2) into a spinneret for wet extrusion composed of 3000 holes each measuring 65 microns.

The extruded mass of threads passes into a coagulation bath (3) containing absolute ethanol. It is then moved over transporting rollers into two successive rinsing baths (4 and 5) containing absolute ethanol. The drafting ratio of the first roller is set at zero while the drafting ratio between the other rollers is set at 1.05. Once it has been passed through the rinsing baths, the hank of threads is blown dry with hot air at 45°–50° C. (6) and cut with a roller cutter (7) into 40 mm fibers.

The mass of fibers thus obtained is tipped into a chute leading to a carding/cross lapping machine (9) from which it emerges as a web, 1 mm thick and weighing 40 mg/mq. The web is then sprayed with a solution of HYAFF 11 in dimethylsulfoxide at 80 mg/ml (11), placed in an ethanol coagulation bath (12), in a rinsing chamber (13), and lastly in a drying chamber (14).

Figure 2:
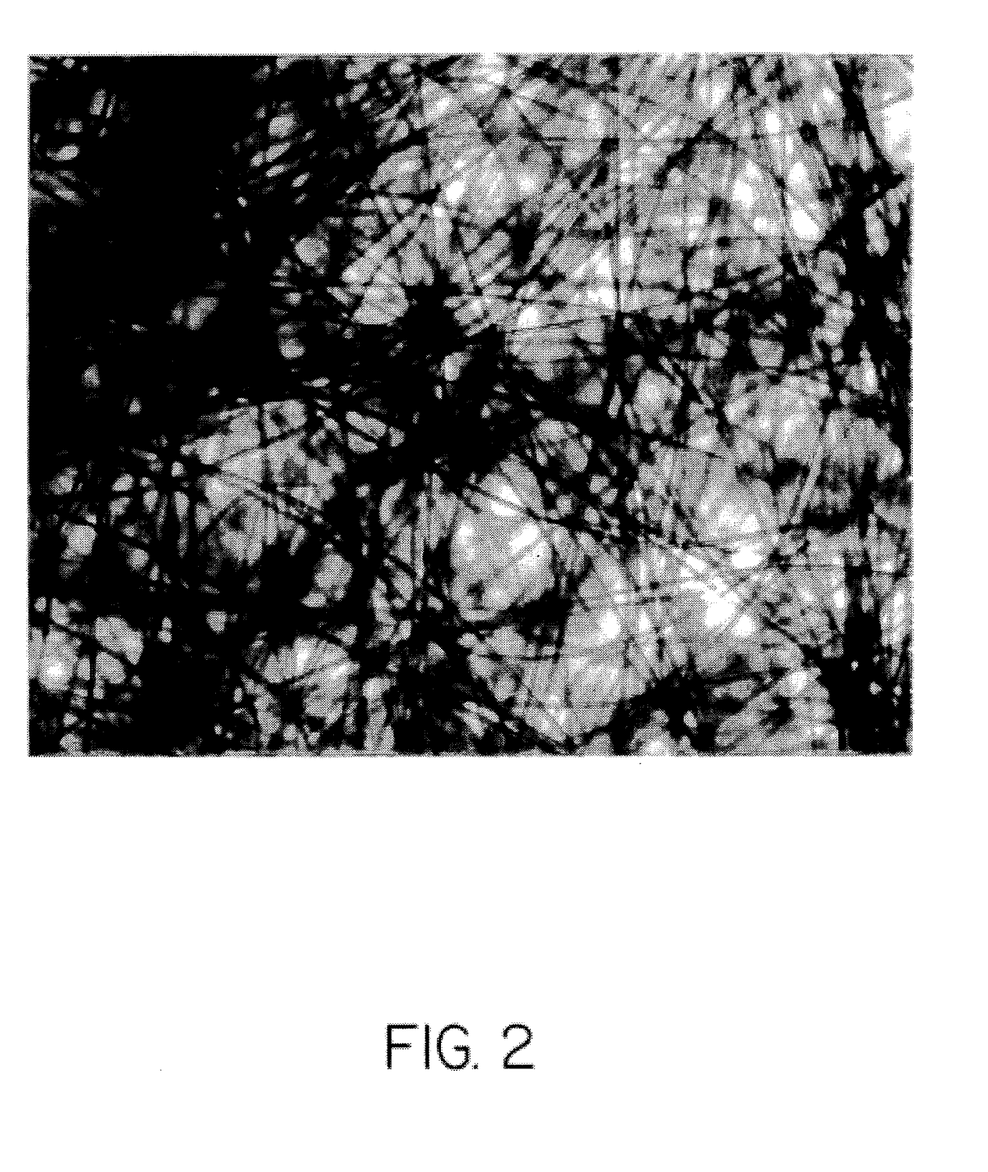
FIG. 2 shows the appearance of the non-woven fabric material comprising the benzyl ester of hyaluronic acid, HYAFF 11, produced in Example 27.

The final thickness of the material is 0.5 mm. Its appearance can be seen in FIG. 2.

EXAMPLE 28

A non-woven fabric comprising the ethyl ester of hyaluronic acid, HYAFF 7, weighing 200 gr/mq and 1.5 mm thick, was produced by the following procedure.

Fibers of HYAFF 7, 3 mm long, obtained by the spinning process described in Example 27, were fed through a chute into a carding machine, from which they emerged as a 1.8 mm thick web weighing 200 gr/mq. The web is passed through a needle punching machine (FIG. 1, details 16, 17, and 18), which transforms it into a non-woven fabric weighing 200 gr/mq, and 1.5 mm thick.

EXAMPLE 29

A non-woven fabric weighing 200 gr/mq and 1.5 mm thick comprising a mixture of the ethyl ester of hyaluronic acid, HYAFF 7, and of hyaluronic acid benzyl ester, HYAFF 11, in equal quantities, was obtained by the following procedure.

Fibers of HYAFF 7 and HYAFF 11, measuring 3 mm in length, obtained by the spinning process described in Example 27 were thoroughly mixed in a spiral mixer. The mixture of fibers was fed into a carding machine from which it emerged as a 1.8 mm thick web weighing 200 gr/mq.

The web was put through a needle punching machine (FIG. 1, details 16, 17, and 18), which transformed it into a 1.5 mm thick unwoven fabric weighing 200 gr/mq, with the two materials perfectly mixed together.

EXAMPLE 30

A non-woven fabric weighing 40 gr/mq and 0.5 mm thick comprising a mixture of hyaluronic acid benzyl ester, HYAFF 11, and a partial (75%) benzyl ester of hyaluronic acid, HYAFF 11p75, in equal percentages, was produced by the following procedure.

HYAFF 11p75 is prepared as follows. 10 g of hyaluronic acid tetrabutylammonium salt, mw=620.76, equal to 16.1 nmole, are solubilized in a mixture of N-methyl pyrrolidone/$H_2O$, 90/10, 2.5% in weight, to obtain 400 mls of solution. The solution is cooled to 10° C., then purified $N_2$ is bubbled through it for 30 minutes. This is then esterified with 1.49 ml (equal to 12.54 mmole) of benzyl bromide. The solution is gently shaken for 60 hours at 15°–20° C.

Subsequent purification is achieved by precipitation in ethyl acetate following the addition of a saturated solution of sodium chloride, and subsequent washings with a mixture of ethyl acetate/absolute ethanol, 80/20. The solid phase is separated by filtration, and treated with anhydrous acetone. 6.8 g of product are thus obtained, equal to a yield of about 95%.

Fibers of HYAFF 11 and HYAFF 11p75, 40 mm long, obtained by the process described in Example 1, were thoroughly mixed in a spiral mixer.

The mixed fibers were fed into a carding machine from which they emerged as a 1 mm thick web weighing 40 mg/mq. The web was then sprayed with a solution of HYAFF 11 in dimethylsulfoxide at 80 mg/ml (FIG. 1, detail 11), placed in an ethanol coagulation bath (12), then in a rinsing chamber (13) containing water or a mixture of water and ethanol in a ratio of from 10 to 95% ethanol, and finally in a drying chamber (14).

The material has a final thickness of 0.5 mm, and the fibers of HYAFF 11 and HYAFF 11p75 are perfectly mixed and adhered together.

EXAMPLE 31

A non-woven fabric comprising the benzyl ester of hyaluronic acid, HYAFF 11, weighing 200 gr/mq and 1.5 mm thick, impregnated with vancomycin, was produced by the following procedure.

The non-woven fabric obtained as described in Example 28 was immersed for 4 hrs in an aqueous solution of vancomycin at a concentration of 0.1 mg/ml. Subsequently, after treatment in a heated colander, the non-woven fabric is dried for 2 hrs in an oven. In vitro release tests showed that the vancomycin is contained in the material in pharmacologically active quantities.

The non-woven fabrics of the present invention can be advantageously utilized in various types of microsurgical procedures, such as in odontology, stomatology, otorhinolaryngology, orthopedics, neurosurgery, etc., in which it is necessary to employ a substance that can be metabolized by the organism and which is capable of facilitating flap take, reepithelialization of mucous membranes, stabilization of grafts, and the filling of cavities. The new nonwoven fabrics can also be employed as buffer media in surgery to the nose and inner ear.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A non-woven fabric material, comprised of fibers of at least one hyaluronic acid ester or at least one hyaluronic acid ester in combination with fibers of another polymer.

2. The non-woven fabric material of claim 1, wherein said polymer is a member selected from the group consisting of collagen, a coprecipitate of collagen and a glycosaminoglycan, cellulose, a polysaccharide in the form of a gel, a semisynthetic derivative of a polymer, a synthetic polymer, and mixtures thereof.

3. The non-woven fabric material of claim 2, wherein said polysaccharide in the form of a gel is a natural gum.

4. The non-woven fabric material of claim 2, wherein said polysaccharide in the form of a gel is a member selected from the group consisting of chitin, chitosan, pectin, pectic acid, agar, agarose, xanthan gum, gellan, alginic acid, an alginate, polymannan, a polyglycan, and a starch.

5. The non-woven fabric material of claim 2, wherein said semisynthetic derivative of a polymer is a member selected from the group consisting of chemically cross-linked collagen, a derivative of cellulose, a derivative of alginic acid, a derivative of a starch, a derivative of chitin, a derivative of chitosan, a derivative of gellan, a derivative of xanthan, a derivative of pectin, a derivative of pectic acid, a derivative of a polyglycan, a derivative of polymannan, a derivative of agar, a derivative of agarose, a derivative of a natural gum, and a derivative of a glycosaminoglycan.

6. The non-woven fabric material of claim 2, wherein said synthetic polymer is a member selected from the group consisting of polylactic acid, polyglycolic acid, a copolymer of polylactic acid and polyglycolic acid, a copolymer of a derivative of polylactic acid and a derivative of polyglycolic acid, a polydioxane, a polyphosphazene, a polysulfone resin, and a polyurethane resin.

7. The non-woven fabric material of claim 1, wherein said hyaluronic acid ester is present alone, or in combination with other hyaluronic acid esters.

8. The non-woven fabric material of claim 1, wherein said hyaluronic acid ester is the ethyl ester of hyaluronic acid.

9. The non-woven fabric material of claim 1, wherein said hyaluronic acid ester is the benzyl ester of hyaluronic acid.

10. The non-woven fabric material of claim 1, wherein said non-woven fabric material comprises a mixture of the ethyl ester of hyaluronic acid and the benzyl ester of hyaluronic acid.

11. The non-woven fabric material of claim 1, wherein said non-woven fabric material comprises a mixture of the benzyl ester of hyaluronic acid and a partial benzyl ester of hyaluronic acid.

12. The non-woven fabric material of 11, wherein said partial benzyl ester of hyaluronic acid is a 75% benzyl ester.

13. The non-woven fabric material of claim 1, wherein said non-woven fabric material is impregnated with a pharmacologically active substance.

14. The non-woven fabric material of claim 13, wherein said pharmacologically active substance is an antibiotic.

15. The non-woven fabric material of claim 14, wherein said antibiotic is vancomycin.

16. The non-woven fabric material of claim 1, weighing between about 20 gr/mq and about 500 gr/mq, having a thickness between about 0.2 mm and about 5 mm, a diameter of the fibers between about 12 microns and about 60 microns, and a length of the fibers between about 5 mm and about 100 mm.

17. The non-woven fabric material of claim 1, weighing about 40 gr/mq, having a thickness of about 0.5 mm, a diameter of the fibers of about 20 microns, and a length of the fibers of about 40 mm.

18. The non-woven fabric material of claim 1, weighing about 200 gr/mq, having a thickness of about 1.5 mm, a diameter of the fibers of about 20 microns, and a length of the fibers of about 3 mm.

19. The non-woven fabric material of claim 1, wherein the residual humidity is between about 0.01 and about 10%.

20. The non-woven fabric material of claim 1, wherein said non-woven fabric material is subjected to chemical cohesive treatment, mechanical cohesive treatment, or treatment with a bonding agent.

21. The non-woven fabric material of claim 20, wherein said chemical cohesive treatment comprises soaking in a solvent, followed by coagulation.

22. The non-woven fabric material of claim 20, wherein said mechanical cohesive treatment comprises needle punching treatment.

23. A non-woven fabric material, comprised of fibers of at least one partial hyaluronic acid ester or at least one partial hyaluronic acid ester in combination with fibers of another polymer.

24. The non-woven fabric material of claim 23, wherein said partial hyaluronic acid ester is a partial benzyl ester of hyaluronic acid.

* * * * *